United States Patent
Whiteside et al.

(10) Patent No.: US 9,855,154 B2
(45) Date of Patent: *Jan. 2, 2018

(54) POST-OPERATIVE RESIDUAL LIMB SUPPORT

(71) Applicant: Hanger, Inc., Austin, TX (US)

(72) Inventors: Stacey A. Whiteside, Chandler, AZ (US); Steven D. Miller, Midway, GA (US)

(73) Assignee: Hanger, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/989,226

(22) Filed: Jan. 6, 2016

(65) Prior Publication Data

US 2016/0113785 A1 Apr. 28, 2016

Related U.S. Application Data

(63) Continuation of application No. 13/917,537, filed on Jun. 13, 2013, now Pat. No. 9,265,630.

(60) Provisional application No. 61/659,839, filed on Jun. 14, 2012.

(51) Int. Cl.
*A61F 2/80* (2006.01)
*A61F 2/78* (2006.01)
*A61F 2/60* (2006.01)

(52) U.S. Cl.
CPC .............. *A61F 2/7812* (2013.01); *A61F 2/80* (2013.01); *A61F 2002/607* (2013.01)

(58) Field of Classification Search
CPC .. A61F 2/78; A61F 2/7812; A61F 2002/7862; A61F 2002/7875; A61F 2002/7881
See application file for complete search history.

(56) References Cited

U.S. PATENT DOCUMENTS

| | | | |
|---|---|---|---|
| 4,842,608 A | 6/1989 | Marx et al. | |
| 5,108,455 A | 4/1992 | Telikicherla | |
| 5,211,667 A | 5/1993 | Danforth | |
| 5,507,722 A | 4/1996 | Richardson | |
| 5,529,575 A | 6/1996 | Klotz | |
| 5,571,209 A | 11/1996 | Brown, Sr. | |
| 5,653,766 A | 8/1997 | Naser | |
| 5,728,165 A | 3/1998 | Brown, Sr. | |
| 7,344,567 B2 | 3/2008 | Slemker | |
| 7,922,773 B1 | 4/2011 | Kuiken | |
| 8,795,385 B2 * | 8/2014 | Bache | A61F 2/78 623/33 |
| 2010/0082116 A1 | 4/2010 | Johnson et al. | |

OTHER PUBLICATIONS

FLO-TECH product information, May 11, 1995, modified Mar. 2010, 7 pages.

(Continued)

*Primary Examiner* — Bruce E Snow
(74) *Attorney, Agent, or Firm* — Foley & Lardner LLP

(57) ABSTRACT

A post-operative residual limb support assembly includes an upper frame configured to extend about at least a portion of a residual limb; and a lower frame coupled to the upper frame and configured to receive an end of the residual limb. The upper frame and the lower frame are adjustable relative to one another in at least one of a linear and rotational manner.

22 Claims, 16 Drawing Sheets

(56) References Cited

OTHER PUBLICATIONS

U.S. Notice of Allowance for U.S. Appl. No. 13/917,537, dated Sep. 28, 2015, 6 pages.
U.S. Office Action for U.S. Appl. No. 13/917,537, dated Jun. 9, 2015, 7 pages.
U.S. Office Action for U.S. Appl. No. 13/917,537, dated Apr. 1, 2015, 12 pages.

\* cited by examiner

US 9,855,154 B2

POST-OPERATIVE RESIDUAL LIMB SUPPORT

CROSS-REFERENCE TO RELATED PATENT APPLICATIONS

This application is a continuation of and claims priority to U.S. patent application Ser. No. 13/917,537, entitled "POST-OPERATIVE RESIDUAL LIMB SUPPORT," filed on Jun. 13, 2013, which claims the benefit of U.S. Provisional Application No. 61/659,839, filed on Jun. 14, 2012, both of which are incorporated herein by reference in their entireties and for all purposes.

BACKGROUND

The present disclosure relates generally to the field of post-operative residual limb supports, and more specifically, to post-operative residual limb supports that may provide improved fit and function for users.

SUMMARY

One embodiment relates to a post-operative residual limb support assembly comprising an upper frame configured to extend about at least a portion of a residual limb; and a lower frame coupled to the upper frame and configured to receive an end of the residual limb; wherein the upper frame and the lower frame are adjustable relative to one another in at least one of a linear and rotational manner.

Another embodiment relates to a post-operative residual limb support assembly comprising an upper frame, the upper frame comprising a pair of extensions extending from a central portion of the upper frame and configured to extend at least partially about the circumference of a residual limb; a lower frame, the lower frame comprising a cup-shaped bottom having first and second sides separated by a slot such that the first and second sides are independently deflectable to accommodate an end of the residual limb; a connection member coupling the upper frame to the lower frame and received in first and second recesses formed in the upper and lower frames, respectively, the connection member and the first and second recesses providing longitudinal and angular adjustment of the upper and lower frames relative to the connection member; and a liner assembly coupled to at least one of the upper frame and the lower frame, the liner assembly configured to be at least partially disposed between the residual limb and the upper and lower frames.

Another embodiment relates to a post-operative residual limb support assembly comprising an upper frame, the upper frame comprising a pair of extensions extending from a central portion of the upper frame and configured to extend at least partially about the circumference of a residual limb, the upper frame further comprising an elongated first connecting portion; a lower frame, the lower frame comprising a cup-shaped bottom having first and second sides separated by a slot such that the first and second sides are deflectable to accommodate an end of the residual limb, the lower frame further comprising an elongated second connecting portion; and a liner assembly coupled to at least one of the upper frame and the lower frame, the liner assembly configured to be at least partially disposed between the residual limb and the upper and lower frames; wherein the first and second connecting portions are usable to couple the upper frame to the lower frame and to provide at least one of longitudinal and angular adjustment of the upper frame relative to the lower frame.

Yet another embodiment relates to a method for fitting a post-operative residual limb support assembly for a patient, the method comprising providing a first frame configured to extend at least partially around a portion of a residual limb; providing a second frame configured to receive at least a portion of the end of the residual limb; adjusting the first frame relative to the second frame to a desired configuration to correspond to a length and a varus/valgus condition of the residual limb; and securing the first frame relative to the second frame in the desired configuration.

DETAILED DESCRIPTION OF EXEMPLARY EMBODIMENTS

Referring to the figures generally, post-operative residual limb support assemblies are often used shortly after amputation of a limb such as a lower portion of a leg (e.g., such as in the case of a transtibial, or below-knee (BK), amputation procedure). Such a device is sometimes referred to as an Immediate Post-Operative Prosthesis (IPOP). After amputation, there is typically a period of time prior to the patient being fitted with a permanent prosthesis. During this time, it is desirable to provide proper support and protection to the residual limb, so as to protect the patient from injury, permit the residual limb to heal properly, and to prepare the residual limb for a permanent prosthesis. If not properly supported and protected, the residual limb may swell and/or take on undesirable shapes. Further, patients sometimes fall after forgetting that a limb has been amputated and that they are now missing a lower portion of a leg. A lack of support and/or protection for the residual limb may result in other undesirable events. As such, various embodiments disclosed herein are directed to providing an improved post-operative residual limb support assembly intended to provide proper support and protection for residual limbs.

Figure 1A:
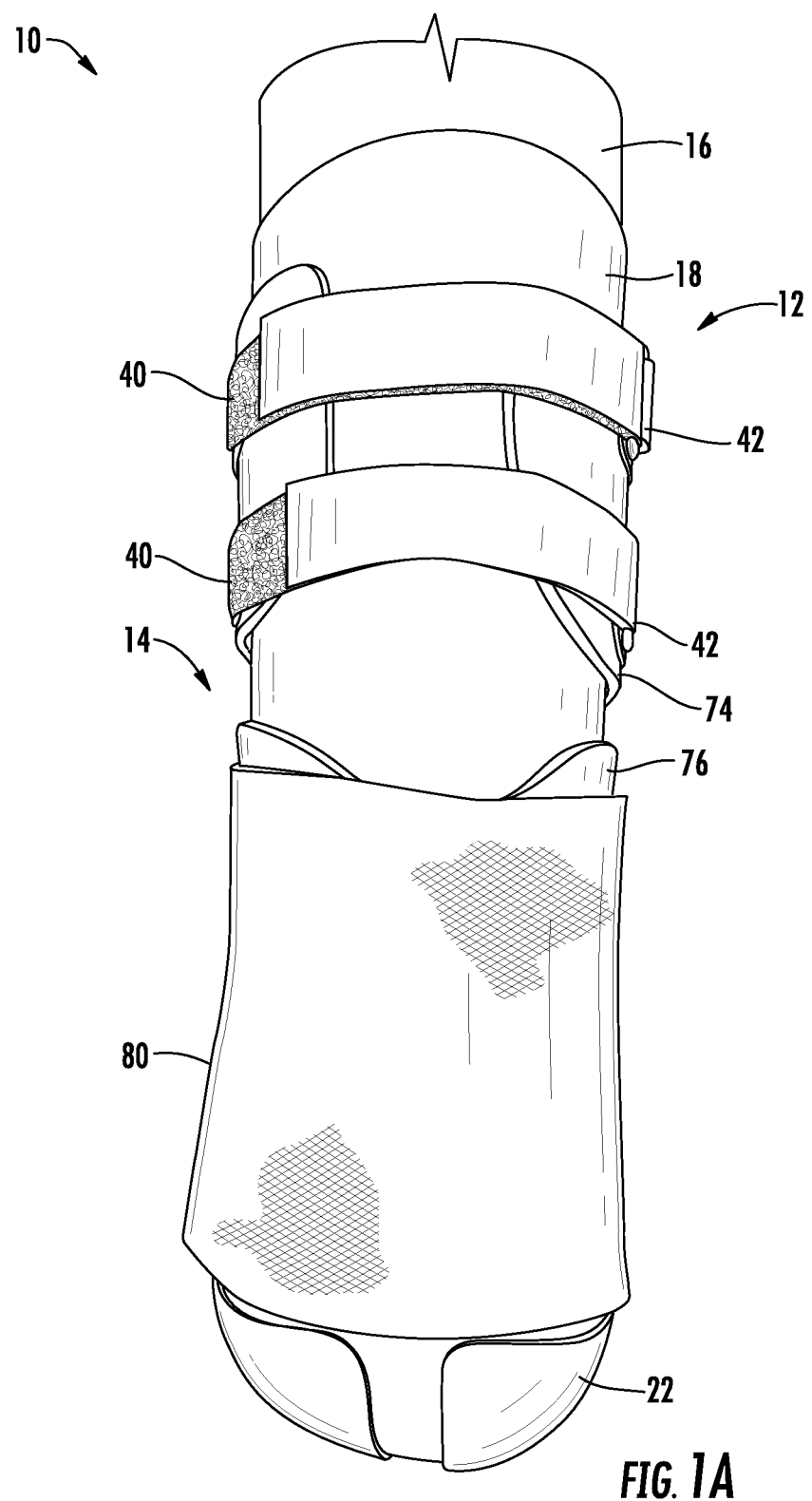
FIG. 1A is a perspective view of a post-operative residual limb support assembly attached to a residual limb according to an exemplary embodiment and FIGS. 1B-1E are additional perspective views thereof.
Figure 1B:
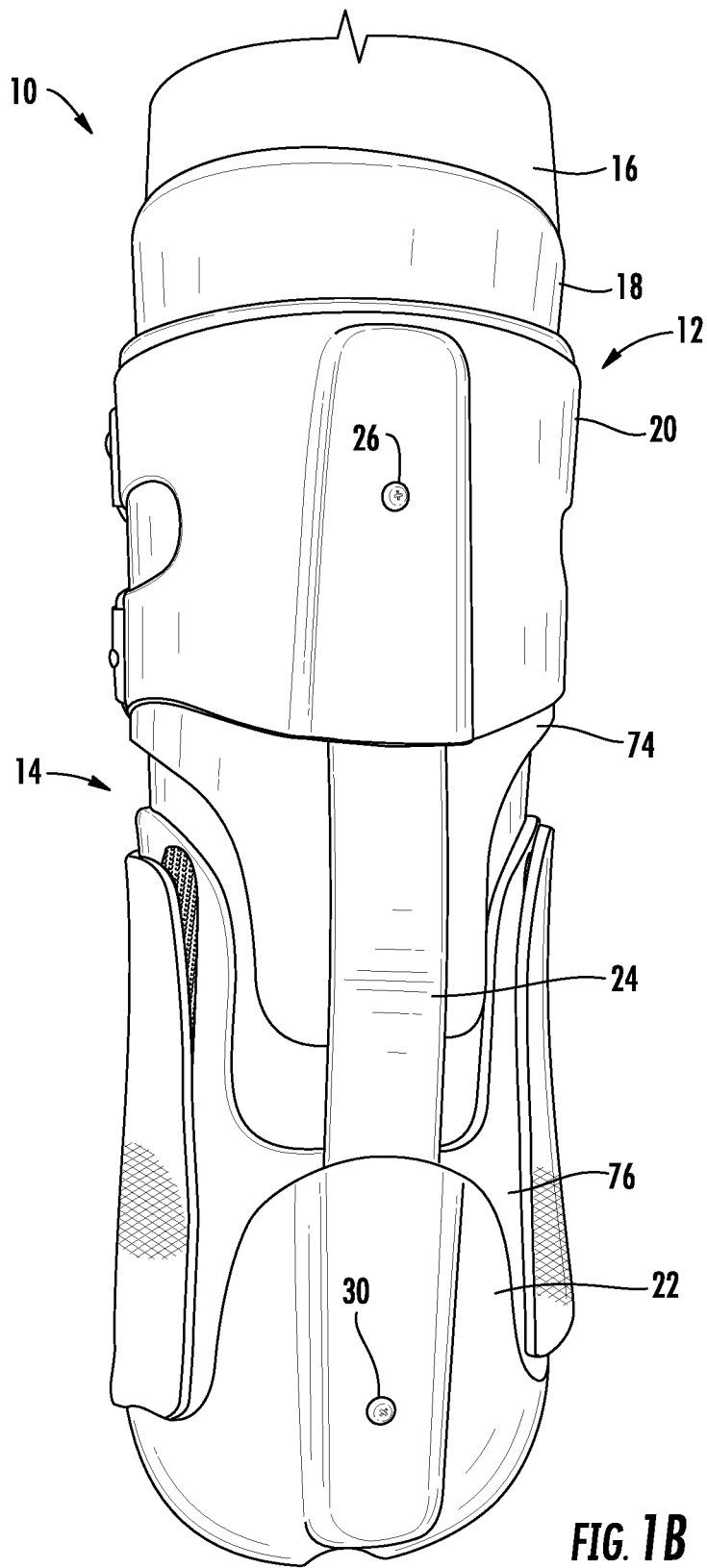

Referring now to FIGS. 1A-4, a post-operative residual limb support assembly is shown as support assembly 10 according to an exemplary embodiment. Support assembly 10 is shown secured to a residual limb 16 of a patient. Dressings 18 (e.g., bandages, shrinkers, etc.) may be applied to residual limb 16 to facilitate the healing process. As shown in FIG. 1A, support assembly 10 may be used after a BK amputation procedure, although it should be understood that support assembly 10 may be used in connection with other types of amputation procedures and in connection with other limbs according to various alternative embodiments.

According to an exemplary embodiment, support assembly 10 includes a frame assembly 12 and a liner assembly 14. Frame assembly 12 may be a relatively rigid or semi-rigid assembly intended to maintain a residual limb in a desired orientation, position, shape, etc. Liner assembly 14 is received within frame assembly 12, and is intended to provide a comfortable and protective interface between frame assembly 12 and the residual limb. Upon initially fitting support assembly 10 for a patient, frame assembly 12 may be adjustable to provide for variations in limb length and/or varus/valgus conditions between patients.

In one embodiment, frame assembly 12 includes an upper frame or cuff, shown as upper frame 20 (e.g., a first frame, an upper support, etc.), a lower frame, or cup, shown as lower frame 22 (e.g., a second frame, a lower support, etc.), and a connection member 24 (e.g., a strut, metal bar, an elongated member, etc.). According to an exemplary embodiment, upper frame 20 is coupled to lower frame 22 via connection member 24 such that upper frame 20 and/or lower frame 22 can be adjusted in a longitudinal (e.g., lengthwise, linear, etc.) and/or angular (e.g., rotational, etc.) fashion relative to connection member 24 and/or each other. According to an exemplary embodiment, connection member 24 is coupled to upper frame 20 by one or more fasteners (e.g., fastener 26), and is coupled to lower frame 22 by one or more fasteners (e.g., fastener 30). As discussed in further detail below, one or more additional fasteners (not shown) may be utilized after having properly configured frame assembly 12 for a particular patient (e.g., via apertures 66, 72), thereby providing a support assembly that is initially adjustable, but can be secured in a desired configuration after fitting.

In the case of a BK (transtibial) amputation, frame assembly 12 may be configured to be fit to a patient such that upper frame 20 extends about the leg above the knee (e.g., extending about at least a portion of a thigh), lower frame 22 extends about the residual limb below the knee (e.g., extending about at least a portion of a residual tibia bone), and connection member 24 extends between upper frame 20 and lower frame 22 generally behind the knee. It should be noted that due to the design and adjustability of frame assembly 12, support assembly 10 may be used with either a right leg or a left leg of a patient.

Figure 1C:
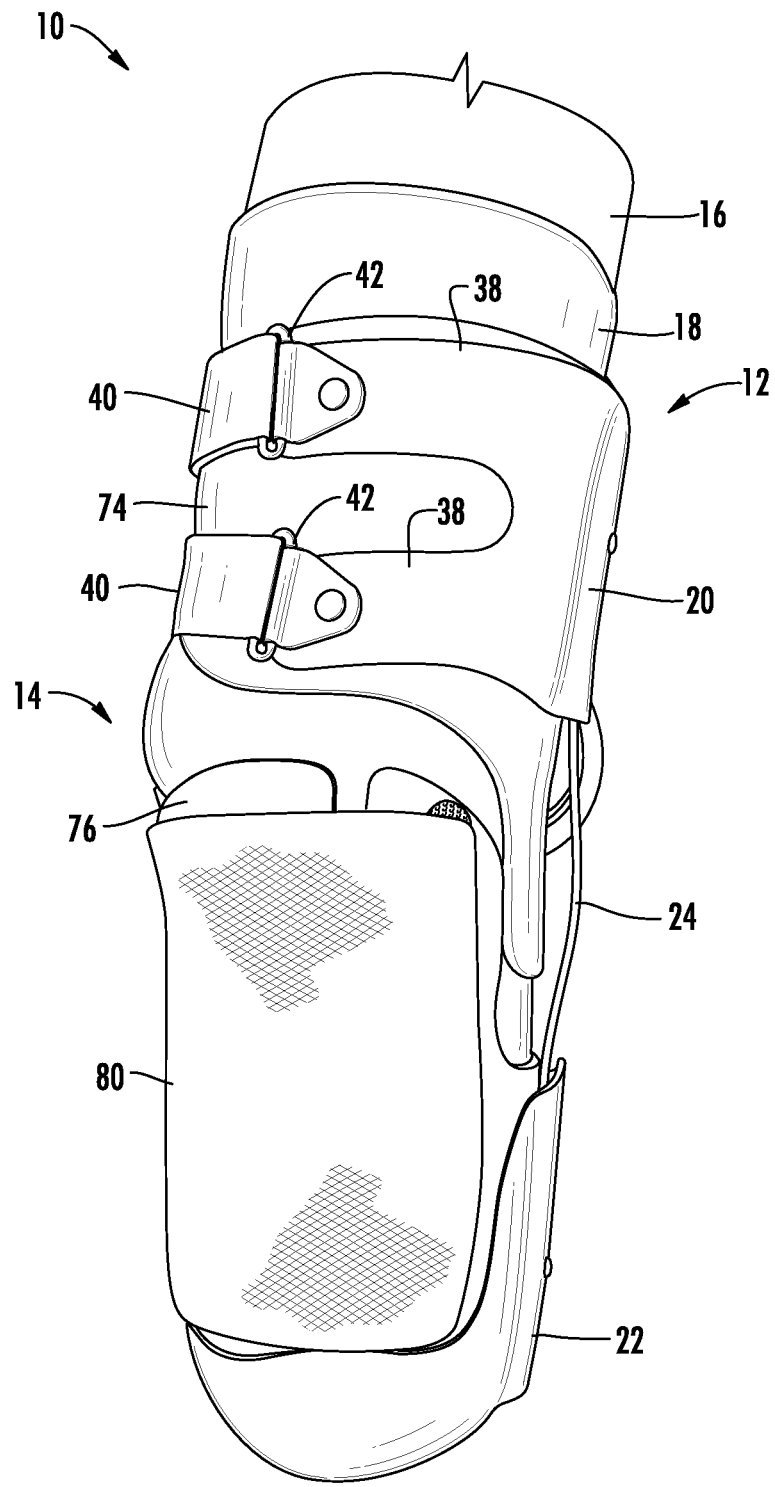
Figure 1D:
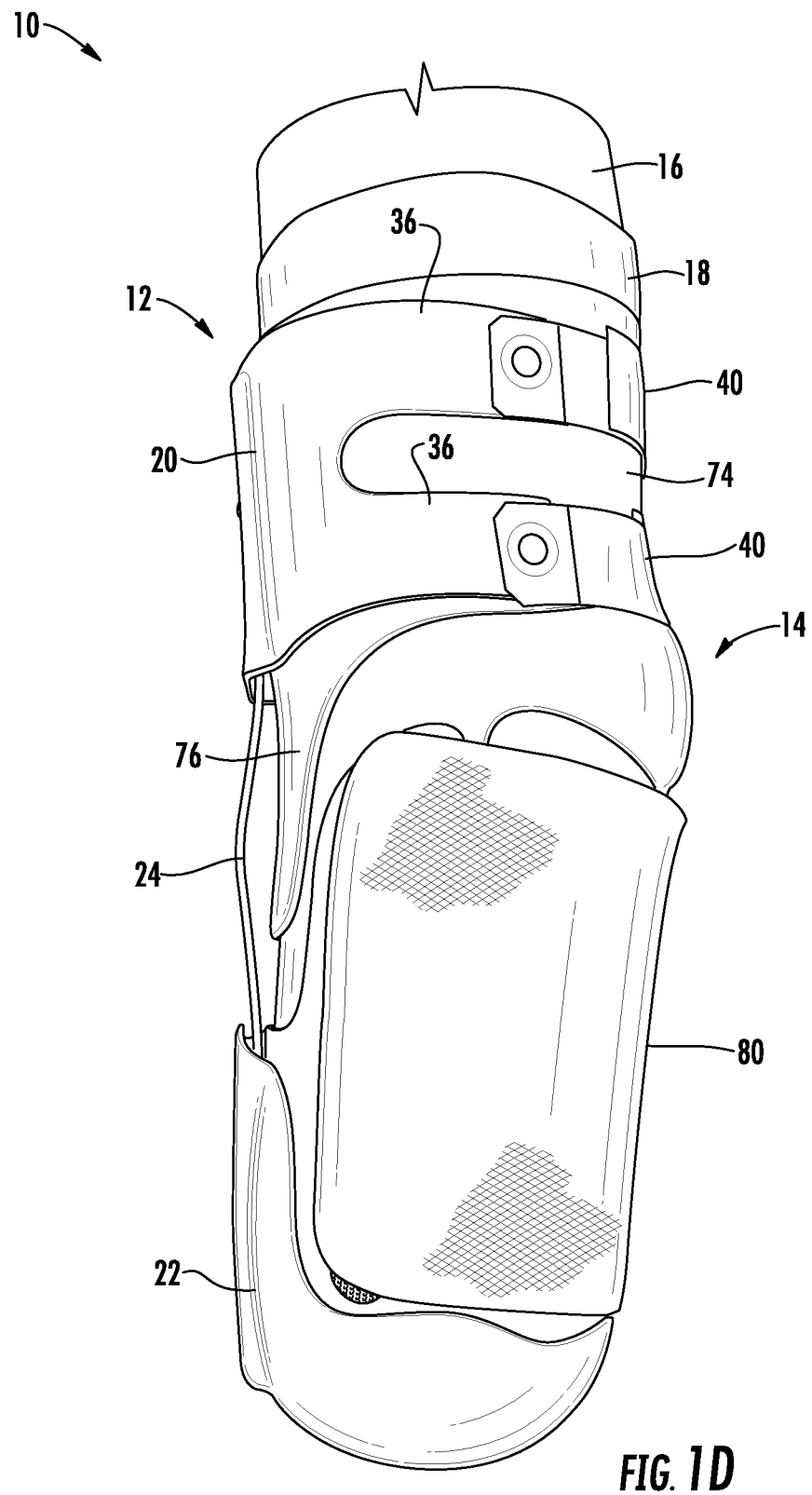

Referring now to FIGS. 1C-1D, according to an exemplary embodiment, upper frame 20 includes a body portion 34 and extensions 36, 38 configured to extend about at least a portion of the residual limb. In some embodiments, extensions 36, 38 are configured to extend about at least a portion of a leg above the knee. One or more straps 40 may extend about all or a portion of extensions 36, 38 or other portions of upper frame 20, and be fastened with strap fasteners 42. Furthermore, one or more attachment pads 44 (e.g., Velcro™ pads or strips, etc.) may be attached to surfaces of upper frame 20 to enable attachment of liner assembly 14 or other components. Straps 40 are configured to create circumferential pressure which suspends and stabilizes upper frame 20. The location and number of straps may be varied depending on the length of upper frame 20.

Figure 2:
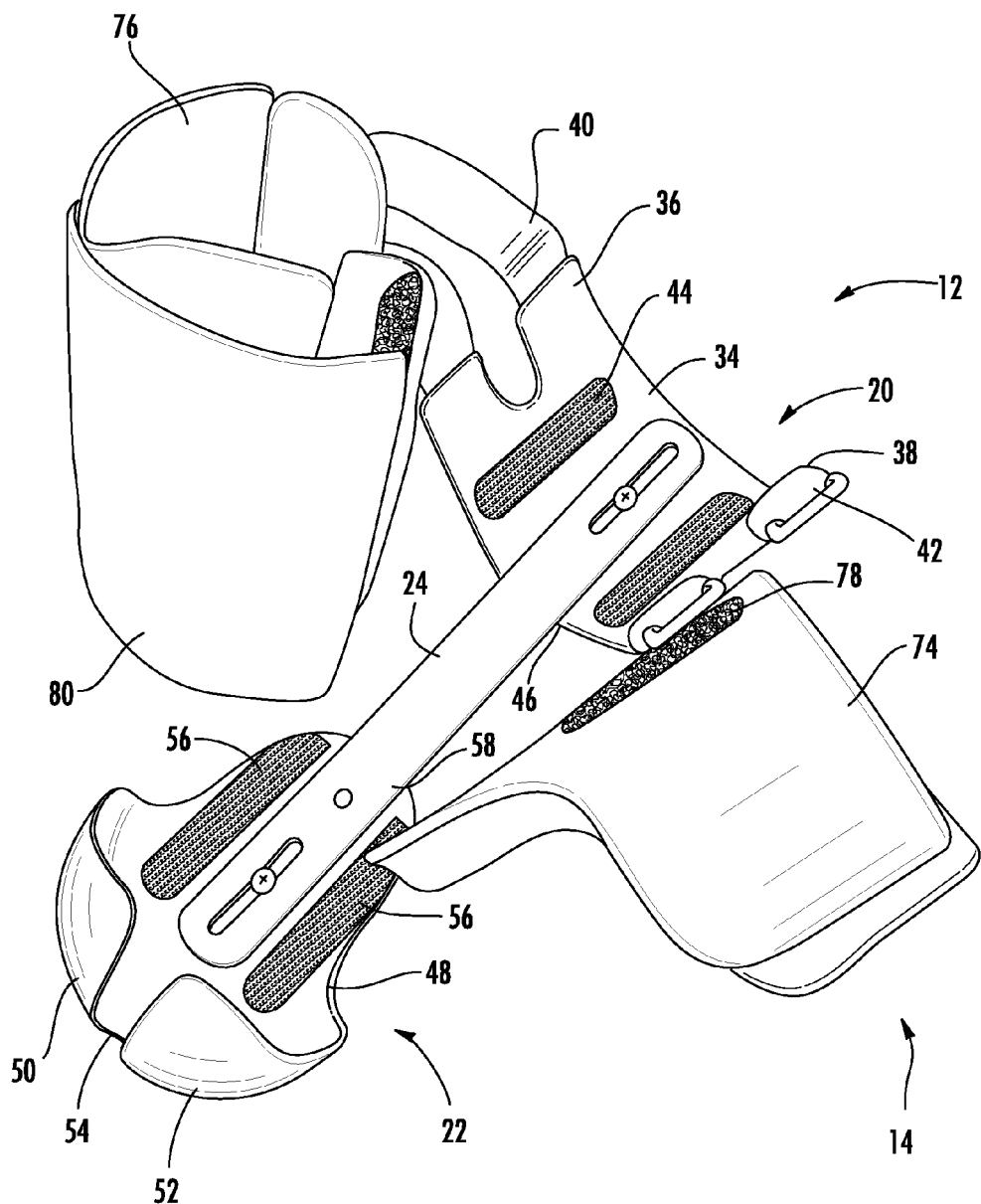
FIG. 2 is an exploded perspective view of the support assembly of FIG. 1 according to an exemplary embodiment.
Figure 3:
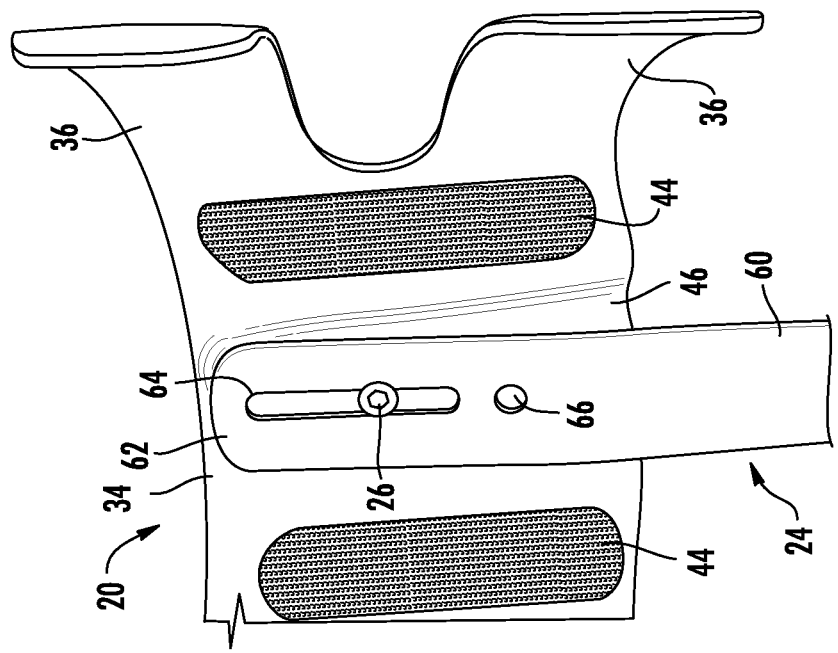
FIG. 3 is a detailed perspective view of a portion of an upper portion frame assembly of the support assembly of FIG. 1A according to an exemplary embodiment.

Referring to FIGS. 2-3, according to an exemplary embodiment, body portion 34 of upper frame 20 defines a recess 46 configured to receive at least a portion of a first end 62 of connection member 24. The sidewall of recess 46 may be tapered along the length of recess 46 such that connection member 24 may be angularly adjusted within recess 46. For example, recess 46 may permit rotation of connection member 24 in either direction up to a predetermined amount (e.g., 5 degrees, 10 degrees, etc.). In some embodiments, recess 46 permits a minimum angular adjustment of 5 degrees in either direction relative to a "straight" position. Inventors: Please confirm these values.

Figure 4:
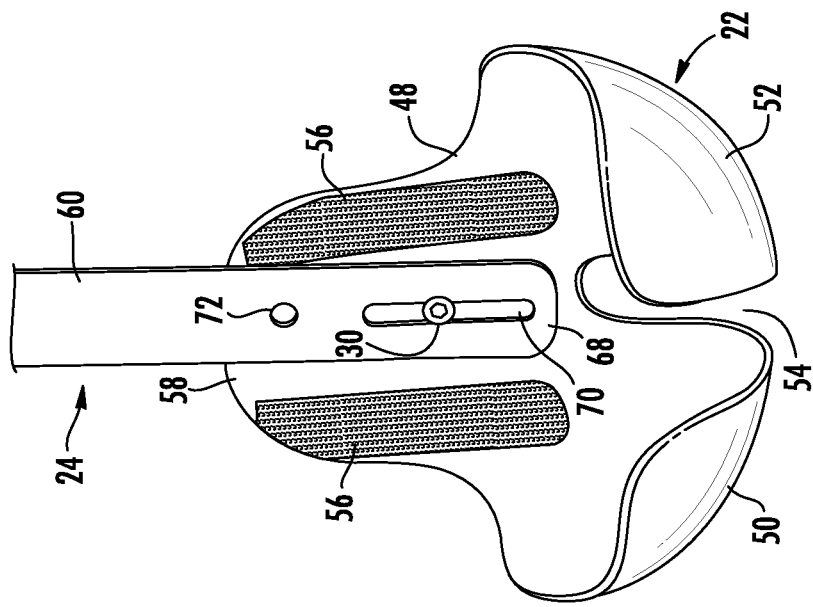
FIG. 4 is a detailed perspective view of a lower portion of a frame assembly of the support assembly of FIG. 1A according to an exemplary embodiment.

Referring now to FIGS. 2 and 4, according to an exemplary embodiment, lower frame 22 includes a body portion 48 having side portions 50, 52 defined by a slot 54. Body portion 48 may form a generally "cup-shaped" interior configured to receive the distal end of the residual limb. Side portions 50, 52 may be semi-spherical in shape, and may be deflectable relative to the remainder of body portion 48 such that side portions 50, 52 can deform (e.g., deflect, bend, etc.) to accommodate the shape of the end of the residual limb (e.g., in the case of angular amputations, irregularities in shape of the residual limb, swelling, etc.). One or more attachment pads 56 (e.g., Velcro™ pads or strips, etc.) may be attached to surfaces of lower frame 22 to enable attachment of liner assembly 14 or other components.

According to an exemplary embodiment, body portion 48 of lower frame 22 defines a recess 58 configured to receive at least a portion of a second end 68 of connection member 24. The sidewall of recess 58 may be tapered along the length of the recess such that connection member 24 may be angularly adjusted within recess 58. For example, recess 58 may permit rotation of connection member 24 in either direction up to a predetermined amount (e.g., 5 degrees, 10 degrees, etc.). In some embodiments, recess 58 permits a minimum angular adjustment of 5 degrees in either direction relative to a "straight" position.

In some embodiments, recesses 46, 58 and connection member 24 may be further sized to provide any desired amount of lengthwise adjustment between components. For example, in one embodiment, connection member 24 may be adjusted relative to upper and lower frames 20, 22 to provide up to 4 inches of lengthwise adjustment (e.g., between a "shortest" configuration of frame assembly 12 and a "longest" configuration of frame assembly 12).

According to an exemplary embodiment, upper frame 20 and/or lower frame 22 are made of a rigid or semi-rigid plastic (e.g., a polyethylene, moldable plastic, etc.). According to other alternative embodiments, upper frame 20 and/or lower frame 22 may be made from any of a variety of suitable materials (e.g., plastics, metals, composites, etc.). Upper and lower frames 20, 22 may be made using any suitable process (e.g., a stamping process and a subsequent molding/forming process, an injection molding process, a machining process, combinations thereof, etc.) according to various alternative embodiments.

According to an exemplary embodiment, connection member 24 is an elongated, generally planar member. In various embodiments, connection member 24 may be or comprise a metal (e.g., aluminum, stainless steel, etc.), polymer (e.g., rigid plastic, etc.), and/or composite material. According to one embodiment, connection member 24 is generally rectangular in shape and may be approximately 16-24 inches long and 0.75-2.5 inches wide, while according to various other embodiments, connection member 24 may take any of a variety of shapes and/or sizes and be of any suitable dimensions. As shown in FIGS. 3-4, connection member 24 may include a first, or upper end 62 having an upper slot 64 and an upper aperture 66, and a second, or lower end 68 having a lower slot 70 and a lower aperture 72. Slots 64, 70 and apertures 66, 72 are configured to provide adjustability between connection member 24 and upper and lower frames 20, 22.

For example, according to an exemplary embodiment, first end 62 of connection member 24 is coupled to upper frame 20 by positioning first end 62 within recess 46 and inserting fastener 26 through upper slot 64 in connection member 24 and through upper frame 20 such that connection member 24 is coupled to upper frame 20 in an adjustable manner (i.e., such that connection member 24 may be rotated and/or moved linearly with respect to fastener 26 and upper frame 20). In a similar manner, second end 68 of connection member 24 may be adjustably coupled to lower frame 22 by using fastener 30. As such, both upper frame 20 and lower frame 22 are initially adjustable with respect to connection member 24. As discussed in further detail below, once upper and lower frames 20, 22 are in a desired configuration relative to connection member 24 for a particular patient, additional fasteners may be used, e.g., apertures 66, 72 to further fasten connection member 24 to upper and lower frames 20, 22 to prevent further undesired relative movement between the components. The fasteners may in some embodiments be rivets, while in other embodiments, other types of fasteners may be used (e.g., t-nuts, threaded fasteners, sliding fasteners, etc.).

Figure 1E:
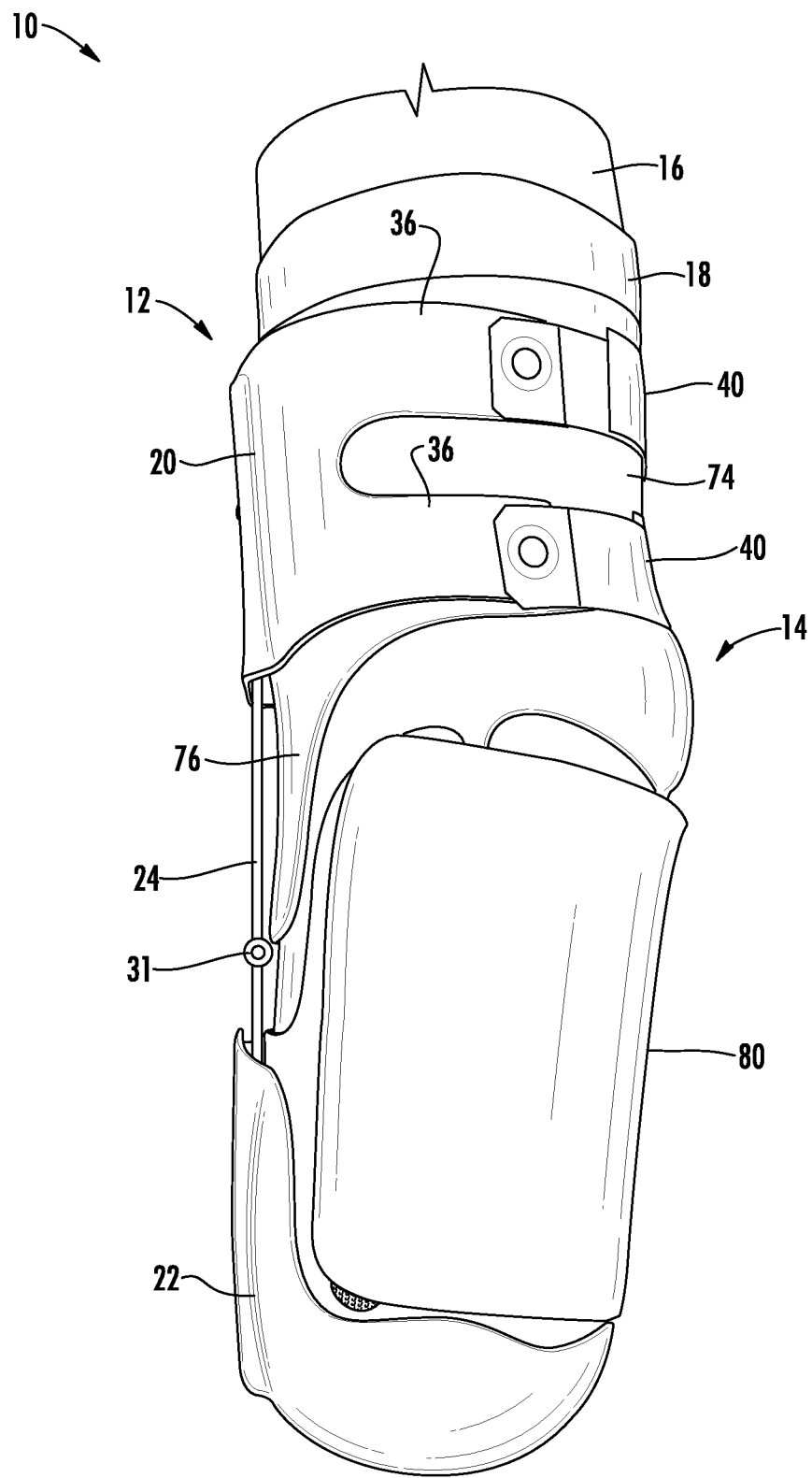

In some embodiments, connection member 24 may be further adjustable to accommodate a desired knee flexion or extension position of the residual limb. For example, as shown in FIGS. 1C-1D, connection member 24 may be configured such that it may be bent (e.g., along its approximate lengthwise midpoint or other location) to correspond to a curvature of the knee resulting from a certain desired amount of knee flexion or extension. Connection member 24 may be configured to be bent (e.g., deformed, deflected, etc.) to any desired angle according to various alternative embodiments. As shown in FIG. 1E, in another embodiment, connection member 24 may include a hinge member 31 or similar component such that an upper portion and a lower portion of connection member 24 are connected by a hinge and the lower portion may pivot relative to the upper portion. A hinged connection member may be utilized, for example, to allow knee flexion or extension for exercises or therapy. In one embodiment, a hinged connection member may allow for incremental ratcheting into extension, locked, and free motion.

According to an exemplary embodiment, liner assembly 14 includes an upper liner 74 and a lower liner 76. One or more pads 78 (e.g., Velcro pads, etc.) may be used to attach upper and lower liners 74, 76 to frame assembly 12. According to an exemplary embodiment, upper liner 74 is removeably coupled to upper frame 20, and lower liner 76 is removeably coupled to lower frame 22. It should be noted that in some embodiments, rather than utilizing discrete upper and lower liners, a single, integral liner assembly may be used and coupled to one or both of upper and lower frames 20, 22. Liner assembly 14 may be made of any suitable material that provides proper comfort and support to patients (e.g., a plastic foam, a compressible polymer, etc.).

According to an exemplary embodiment, upper and lower liners 74, 76 may be sized and shaped to generally conform to the shape of the residual limb. Further, upper and lower liners 74, 76, may be sized such that they extend beyond the periphery of upper and lower frames 20, 22, so as to prevent unwanted friction, scraping, etc., between upper and lower frames 20, 22 and the residual limb. According to various alternative embodiments, upper and lower liners 74, 76 may take any desired shape and/or form and be made of any suitable material.

In general, upper and lower liners 74, 76 are positioned on upper and lower frames 20, 22, respectively. The residual limb, with appropriate dressings applied, is inserted into support assembly 10 and upper and lower liners 74, 76. Straps 40, 80 may then be fastened about support assembly 10 to secure the residual limb within support assembly 10. As shown in FIG. 1A, strap 80 may be a relatively wide elastic member configured to both compress the liners about the residual limb and to provide protection from falls, etc. The length and width of strap 80 may be varied depending on the size of the residual limb.

Figure 5:
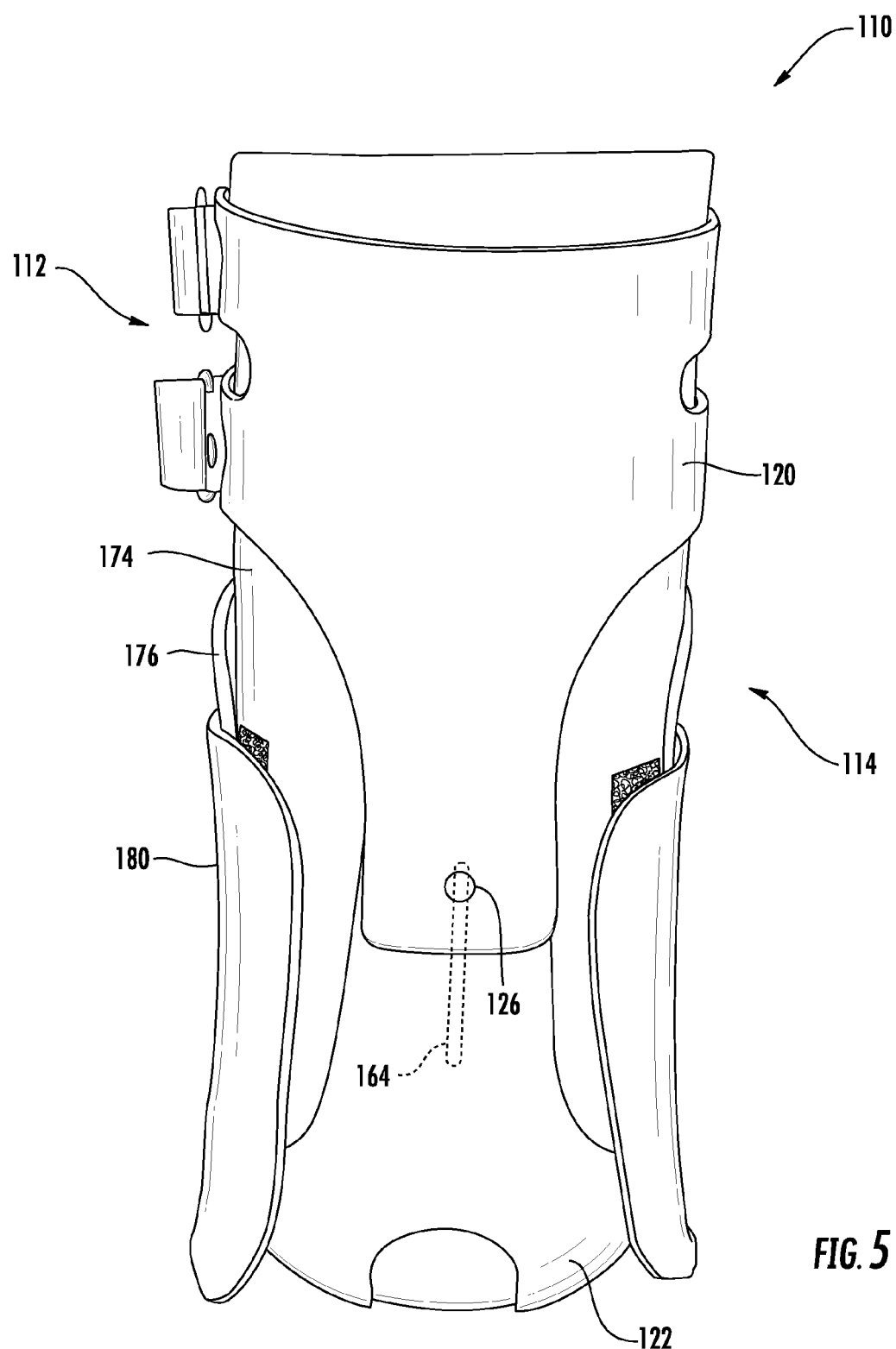
FIG. 5 is a perspective view of a post-operative residual limb support assembly according to another exemplary embodiment.
Figure 6:
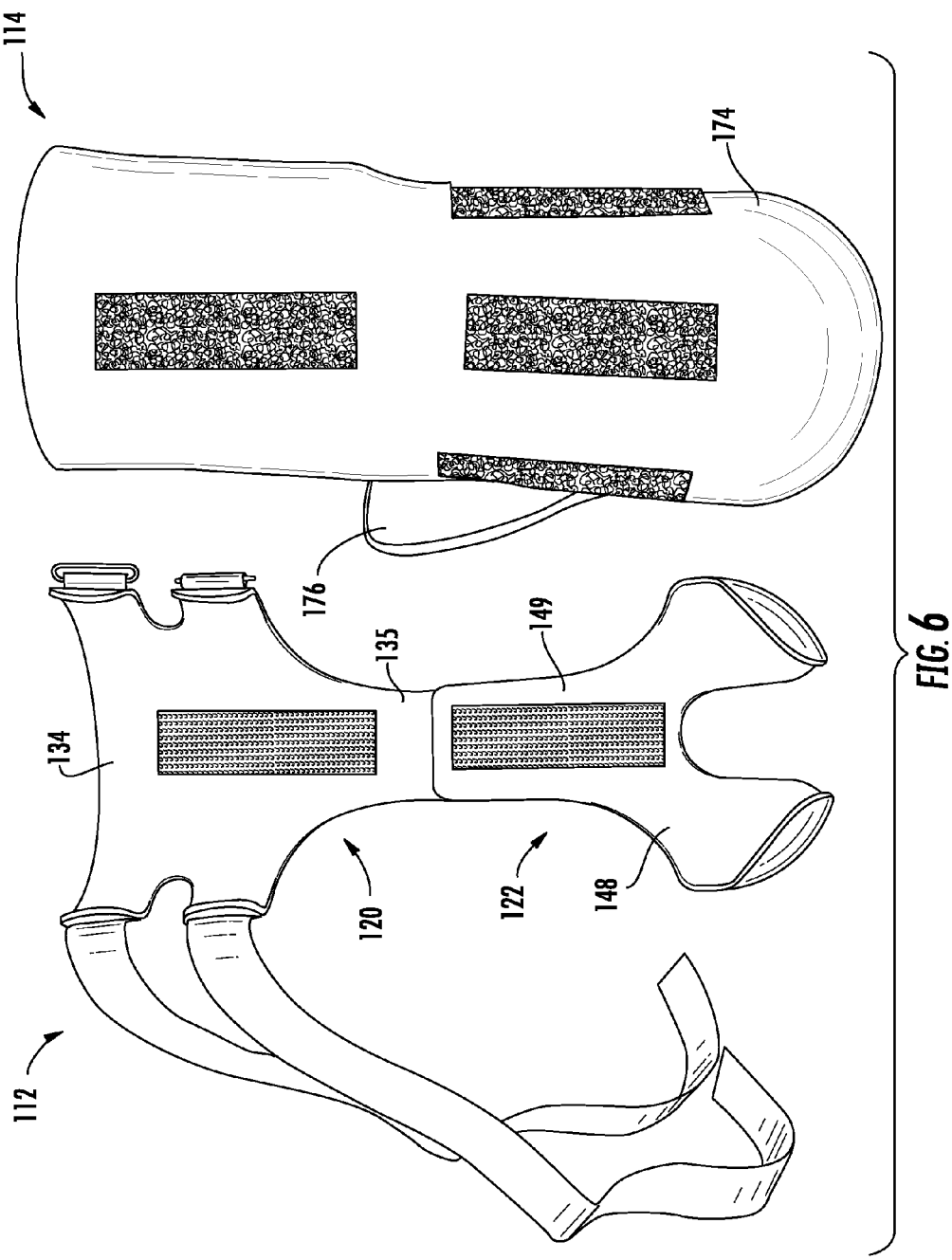
FIG. 6 is an exploded perspective view of the support assembly of FIG. 5 according to an exemplary embodiment.
Figure 7:
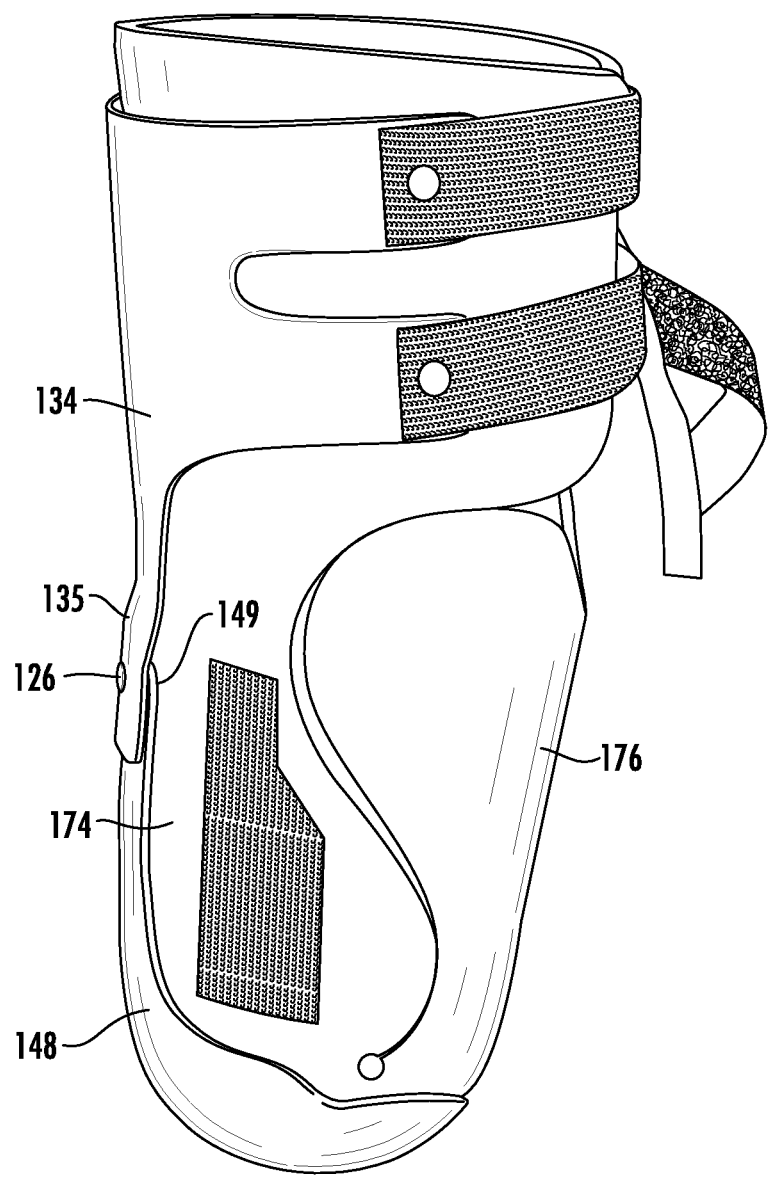
FIG. 7 is a side view of the support assembly of FIG. 4 according to an exemplary embodiment.

Referring now to FIGS. 5-7, a support assembly 110 is shown according to an exemplary embodiment. Support assembly 110 may be in many respects similar to support assembly 10 described herein, and as such many of the features and combinations of features described with respect to support assembly 10 are equally applicable and/or usable in connection with support assembly 110.

According to an exemplary embodiment, support assembly 110 includes a frame assembly 112 and a liner assembly 114. As with frame assembly 12, frame assembly 112 provides both rotational and linear adjustability for fitting support assembly 110 to a particular patient. As discussed below, support assembly 110 may be made as a "custom-fit" device (e.g., for a particular patient), or alternatively, may be configured to be usable with multiple patients (e.g., by adjusting the length/rotational position of the frame components).

As shown in FIGS. 5-7, frame assembly 112 includes an upper frame 120 and a lower frame 122. However, rather than upper frame 120 being coupled to lower frame 122 via a connection member, as with frame assembly 12, upper frame 120 and lower frame 122 are configured to be directly coupled to each other via extension members 135, 149 extending from bodies 134, 148, of upper and lower frames 120, 122, respectively. As shown in FIG. 7, extension member 135 may be a generally elongated member extending downward from body 134, and extension member 149 may be a similarly elongated member extending upward from body 148. Extension members 135, 149 may be configured to easily slide relative to one another (e.g., by having corresponding geometries, etc.). One or both of upper frame 120 and lower frame 122 may include a slot (not shown) for providing adjustability between the frame components. An optional slot 164 may be provided in lower frame 122.

In some embodiments, to provide a "custom-fit" support, upper and lower frames 120, 122 may be made to conform to the size and/or shape of a particular residual limb. For example, based on the size, shape, and/or dimensions of the residual limb, upper and lower frames 120, 122 may be stamped, formed, and/or machined into a shape that is designed for a particular residual limb (e.g., by utilizing a cast of the limb, dimensions of the limb, etc.), thereby minimizing the necessary adjustments to the relative positions of upper and lower frames 120, 122.

In some embodiments, fasteners (e.g., fastener 126) are utilized to fasten upper frame 120 to lower frame 122. For example, upper frame 120 may initially be coupled to lower frame 122 using a single fastener 126 (e.g., within a slot in one of the frame members), such that upper frame 120 may be moved relative to lower frame 122 to a desired configuration for a particular patient (e.g., to accommodate variations in limb length and/or varus/valgus conditions). Upon determining a desired configuration for a patient, a second fastener (not shown) may be utilized to securely fix the relative positions of upper frame 120 and lower frame 122. As with frame assembly 12 and liner assembly 14, liner assembly 114 may be coupled to frame assembly 112 prior to, during, or after the adjustment of frame assembly 112.

In other embodiments, upper and lower frames 120, 122 may be made to be a more "standard" or "off-the-shelf" configuration, size, and/or shape, such that a single size and shape of upper and lower frames 120, 122 can be adjusted to fit a range of residual limb shapes and sizes. In one embodiment, a slot 164 is provided in lower frame 122. Slot 164 may have a length of approximately 4 inches and a width of approximately 0.25 inches. If a varus/valgus angle adjustment is not needed, a second fastener similar to fastener 126 may be provided within slot 164 to fix the relative positions of upper frame 120 and lower frame 122 (e.g., using a T-nut or similar fastener). Furthermore, a range of standard sizes (e.g., small, medium, large, etc.) of each component (e.g., the frame and/or liner components) may be utilized, and standard sizes may be appropriately matched to fit a particular residual limb (e.g., by matching a "large" upper frame with a "small" lower frame, etc.). Further yet, one or both frame members may be heated to accommodate a flexion angle of a patient, and a hinge with incremental adjustment, spring-assisted motion, and/or free motion may be incorporated into one or both frame members or provided as a separate component to provide for knee flexion contracture to be worked out with exercises and/or therapy.

According to an exemplary embodiment, liner assembly 114 is a unitary liner assembly provided with one or more portions 174, 176 that generally conform to the residual limb and that may be defined by one or more slits, or cuts in the liner material that facilitate fitting liner assembly 114 to the residual limb. Furthermore, a strap 180 (e.g., an elastic strap utilizing Velcro-type fasteners, etc.) similar to strap 80 may be utilized to provide additional support around all or a portion of the circumference of liner assembly 114. In one embodiment, strap 180 is positioned to extend about a leg below the knee, and one or more additional straps (e.g., similar to straps 40) may be positioned to extend around the leg above the knee.

Figure 8:
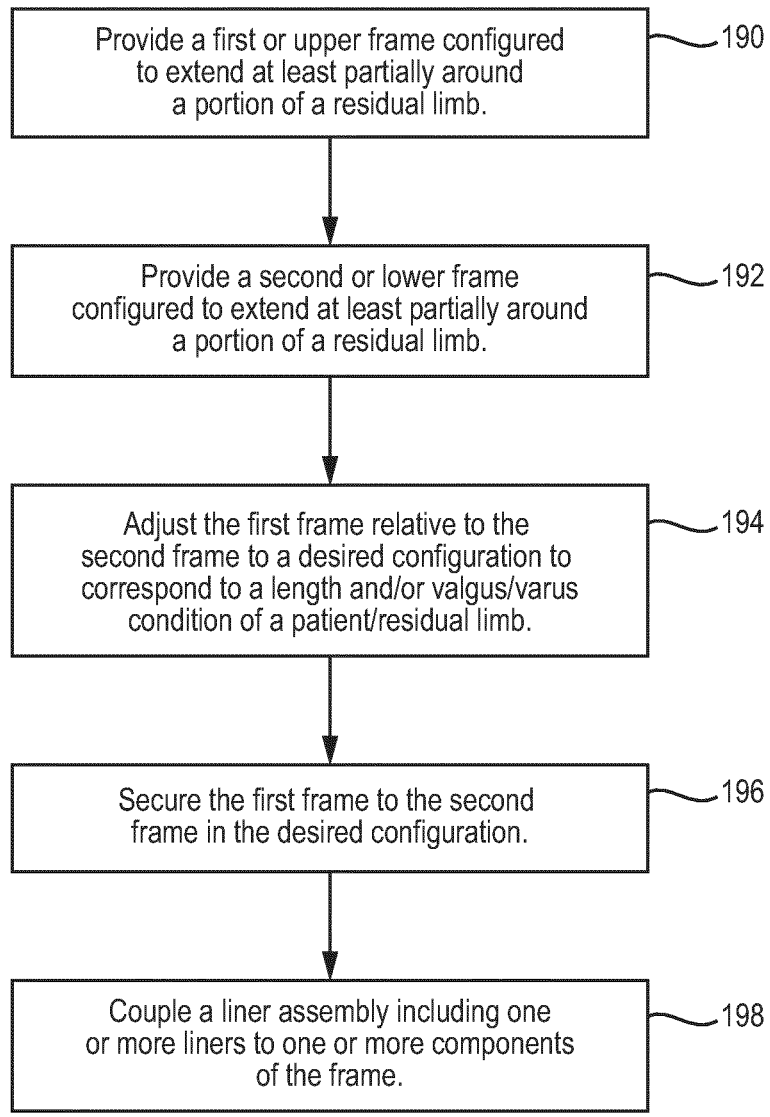
FIG. 8 is a flow chart illustrating a method for configuring a post-operative residual limb support assembly according to an exemplary embodiment.
Figure 9:
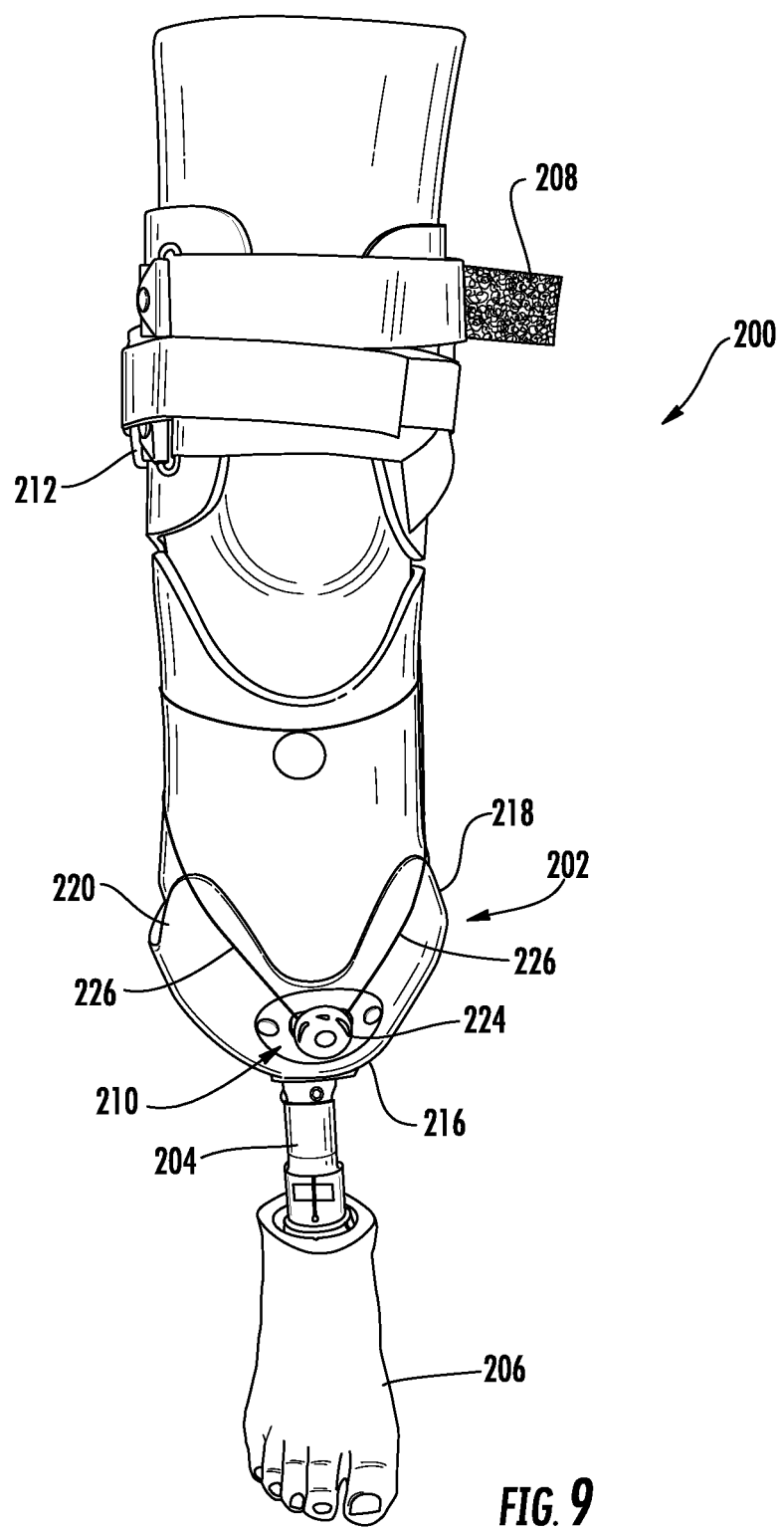
FIG. 9 is a front view of a lower support assembly usable with a support assembly according to an exemplary embodiment.
Figure 10:
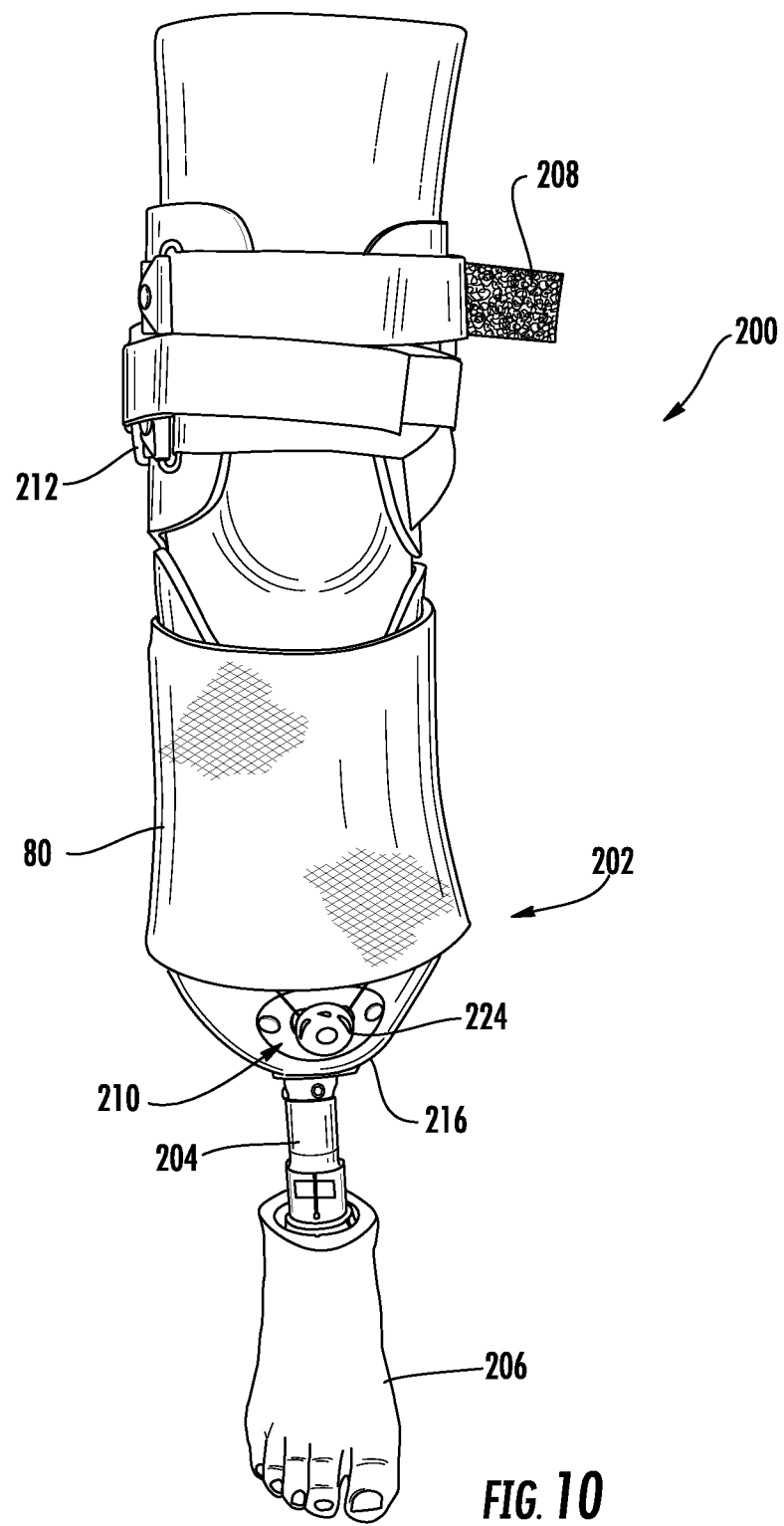
FIG. 10 is another front view of the lower support assembly of FIG. 9 according to an exemplary embodiment.

Referring now to FIG. 8, a method of adjusting a support assembly to fit a patient is shown according to an exemplary embodiment. First, a first or upper frame configured to extend at least partially around a portion of a residual limb is provided (step 190). A second or lower frame configured to receive at least a portion of the end of the residual limb is further provided (step 192). The first frame is adjusted relative to the second frame to a desired configuration to correspond to a length and/or a varus/valgus condition of a patient/residual limb (step 194). Adjusting the first frame relative to the second frame may include, e.g., adjusting one or both of the first frame and the second frame relative to a connection member that couples the first frame to the second frame. After adjusting the first frame relative to the second frame, the first frame is secured relative to the second frame in the desired configuration (step 196). A liner assembly including one or more liners may be coupled to one or more components of the frame at any point during the process (e.g., prior to, during, and/or after adjustment of the frame assembly) (step 198).

Referring to FIGS. 9-13, a lower support assembly 200 usable with a support assembly such as support assembly 10 or support assembly 110 is shown according to one embodiment. As shown in FIGS. 10-13, lower support assembly 200 includes a frame 202, a pylon 204, and an artificial foot 206. Lower support assembly 200 further includes one or more straps 208 (e.g., 1, 2, 3, etc.) and a connector assembly 210. Generally, frame 202 (e.g., a rigid, or semi-rigid frame, support member, etc.) is configured to receive residual limb 16 and support assembly 10. Pylon 204 (e.g., an intermediate support member, an extension, etc.) is coupled to a lower portion of frame 202 and extends between frame 202 and artificial foot 206 (e.g., a prosthetic foot or limb, etc.). Artificial foot 206 is coupled to a lower portion of pylon 204 and is configured to simulate an actual foot of a patient and enable a patient to use lower support assembly 200 to support at least a portion of the patient's body weight.

In order to secure support assembly 10 within lower support assembly 200, one or more straps, connectors, etc. are utilized. For example, as shown in FIGS. 9-13, a strap 208 (e.g., a band, a securing member, etc.) is configured to extend around support assembly 10 and frame 202 to securely hold support assembly 10 within lower support assembly 200. Strap 208 can extend in a circumferential manner about all or a portion of support assembly 10 and/or frame 202 of lower support assembly 200. In one embodiment, strap 208 is configured to be positioned above the knee of a patient, while in other embodiments, strap 208 can be positioned at various other locations along support assembly 10 and/or lower support assembly 200. Strap 208 can include one or more elastic and/or inelastic portions, and can include features such as hook and loop fasteners, etc. to facilitate the use of strap 208. In one embodiment, two straps 208 are used.

Figure 11:
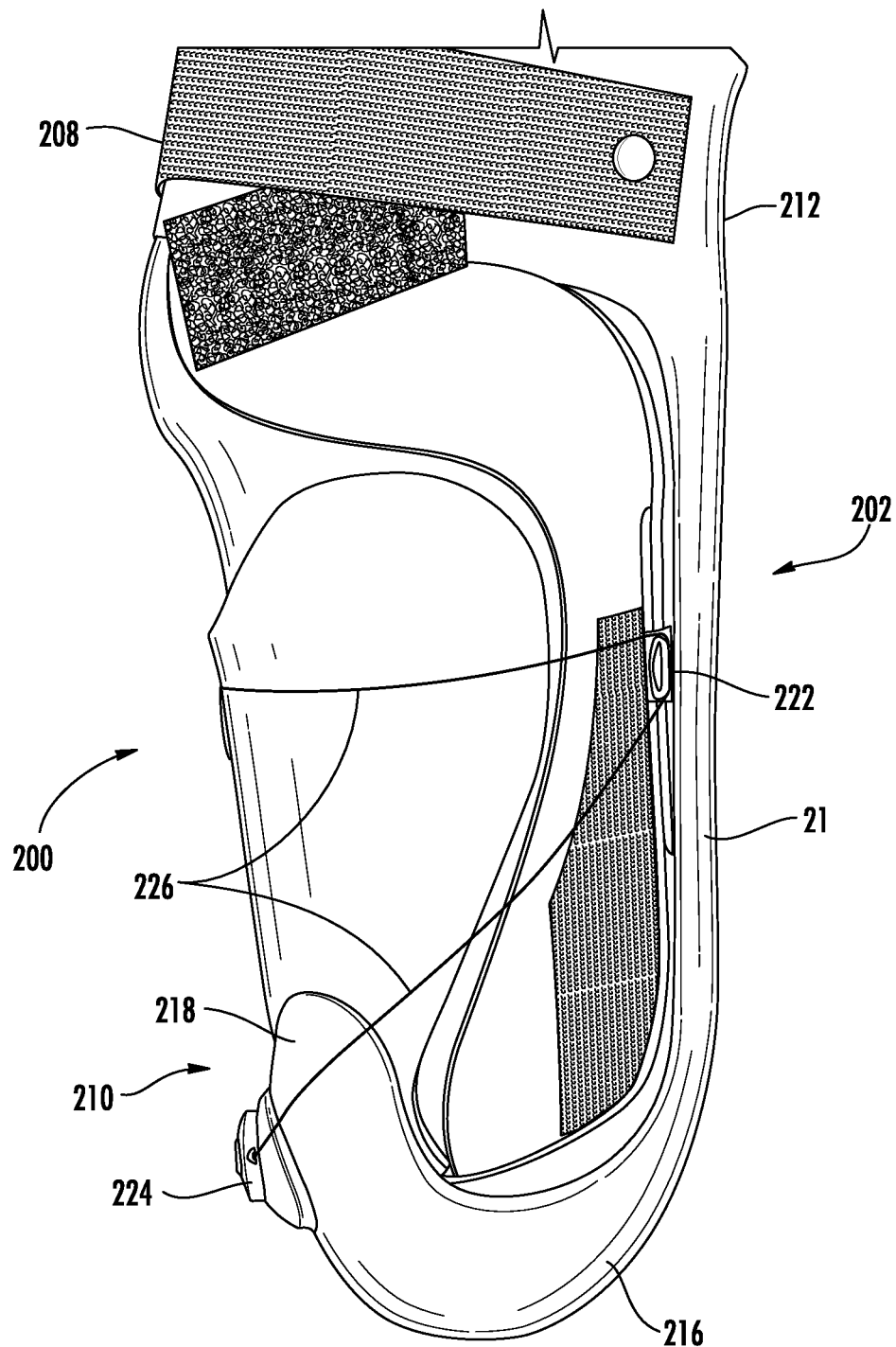
FIG. 11 is a side view of a portion of the lower support assembly of FIG. 9 according to an exemplary embodiment.

To further secure support assembly 10 within lower support assembly 200, a connector assembly 210 is utilized. As shown in FIGS. 9-13, connector assembly includes an adjustment member 224 (e.g., a knob, lever, etc.) and a relatively small diameter cable 226 (e.g., a flexible wire, an elastic, elongated member, a flexible and/or elastic wire, etc.). Member 224 is fixed to a lower portion of frame 202, and cable 226 forms a loop extending from member 224. As shown in FIG. 11, frame 20 includes one or more loops 222 (e.g., hooks, retaining members, clips, etc.) configured to slidably receive cable 226. Cable 226 can be positioned to extend from member 224, upward to loops 222 on generally opposite sides of frame 202, and then across the front of frame 202 and support assembly 10. In one embodiment, member 224 is configured such that rotation of member 224 decreases the length of cable 226, so as to take up any slack in cable 226 and tighten cable 226 against support assembly 10. As such, cable 226 securely holds support assembly 10 within lower support assembly 200. In one embodiment, connector 10 is located such that cable 226 extends across the front of support assembly 10 below the knee of a patient. In other embodiments, connector 10 can be used at other locations along support assembly 10 and/or lower support assembly 200.

Figure 12:
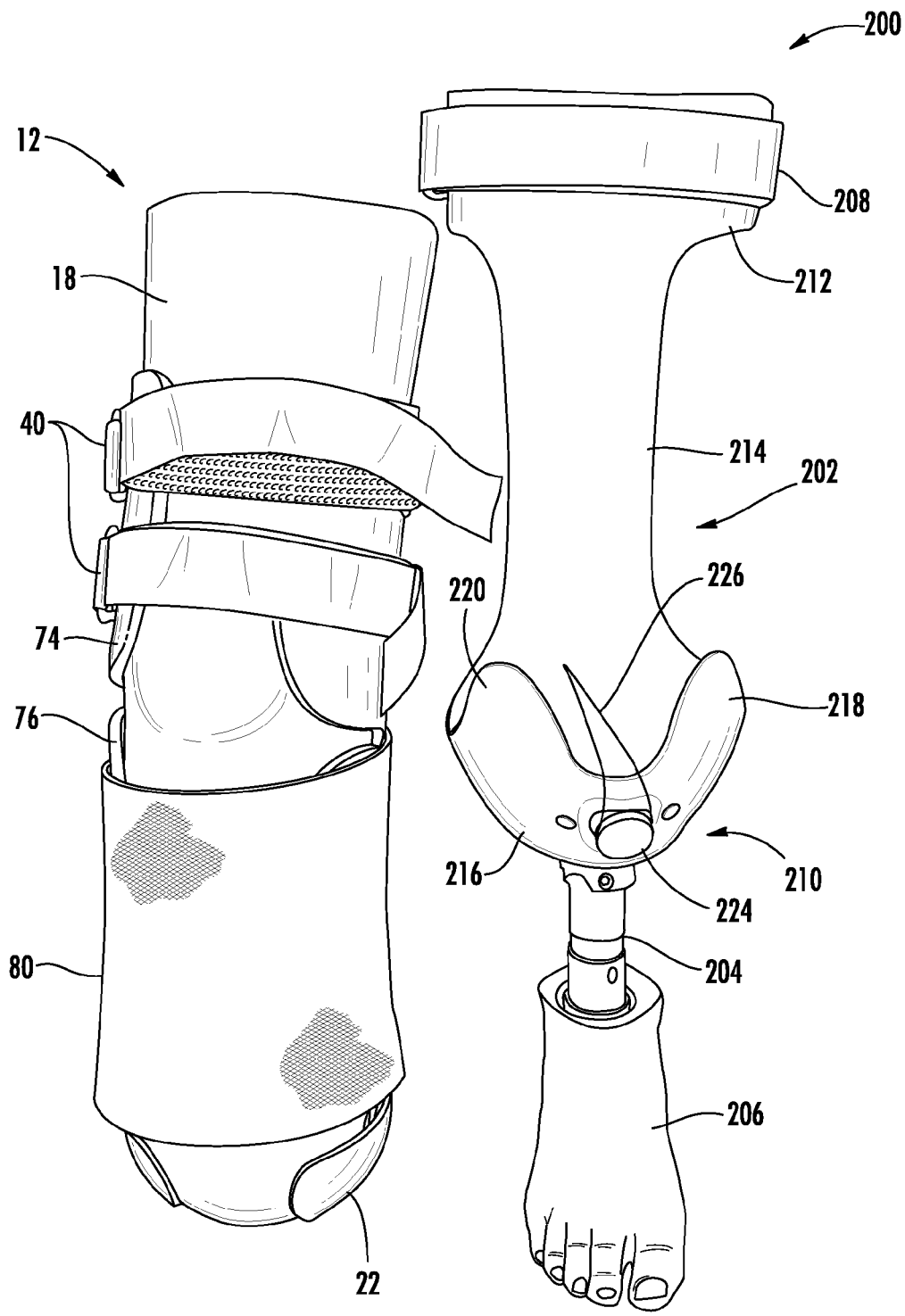
FIG. 12 is a front view of the lower support assembly of FIG. 9 separated from a support assembly according to an exemplary embodiment.
Figure 13:
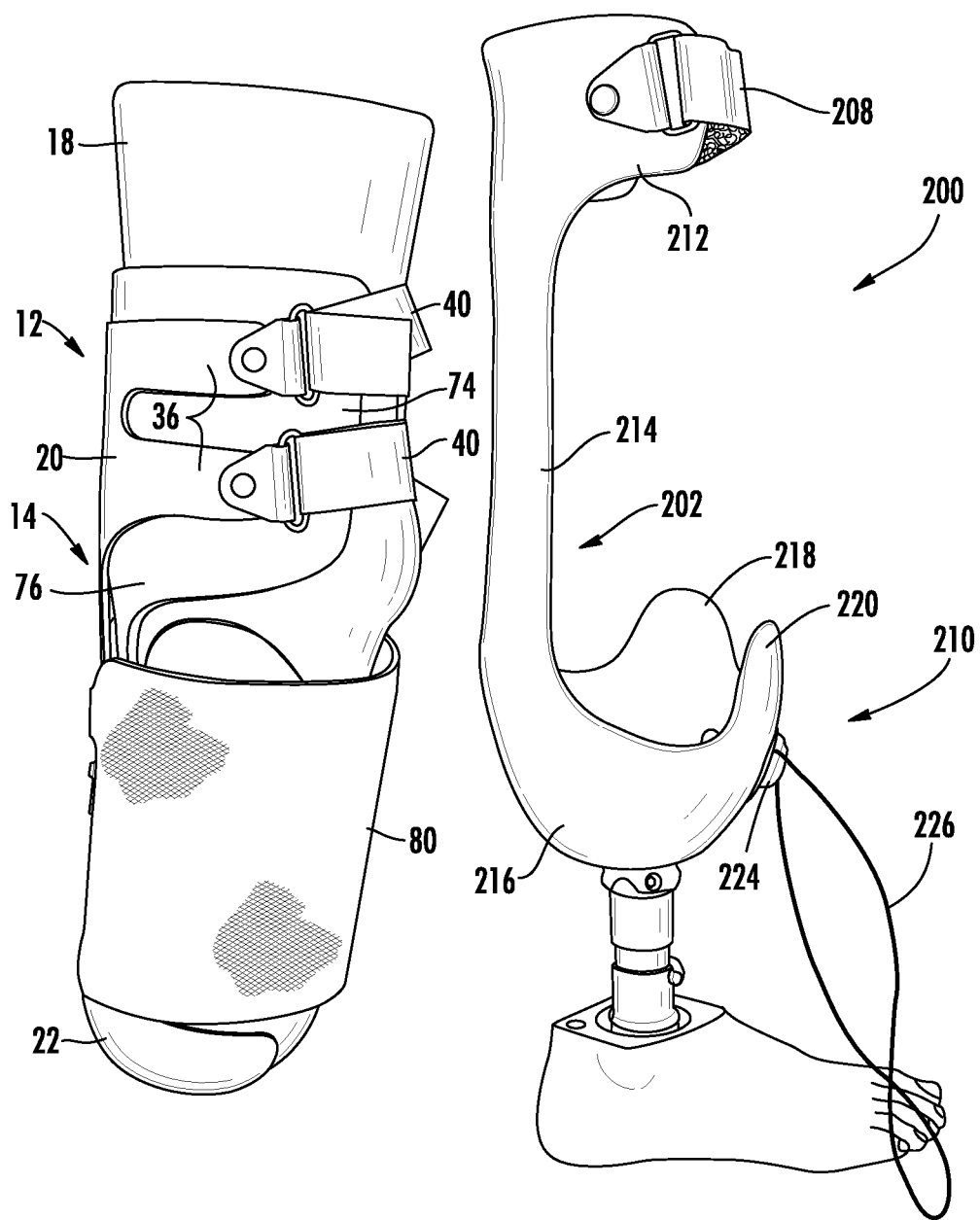
FIG. 13 is a side view of the lower support assembly of FIG. 9 separated from a support assembly according to an exemplary embodiment.

According to one embodiment, frame 202 includes an upper portion 212, an intermediate portion 214, and a lower portion 216. Upper portion 212 is configured to extend about all or a portion of a patient's residual limb and/or support assembly 10 above the knee. Lower portion 216 is configured to receive all or a portion of a bottom portion of a residual limb and is some embodiments generally conforms to the shape of the residual limb. Intermediate portion 214 structurally connects upper portion 212 and lower portion 216. As shown in FIG. 12, lower portion 216 may further include two upwardly-extending contoured portions 218, 220 that are configured to further secure support assembly 10 within lower support assembly 200 (e.g., by preventing forward/outward movement of the lower portion of support assembly 10 and/or the residual limb).

In one embodiment, frame 202 is a substantially rigid member made of a polymer material. Frame 202 can be made using any suitable process, including injection molding, vacuum forming, and the like. In alternative embodiments, all or a portion of frame 202 can be made of a semi-rigid or flexible material. In yet further embodiments, frame 202 includes metal portions and/or polymer/metal composite materials. Any suitable combination of materials can be utilized that provides the proper support and retention of support assembly 10 and the residual limb.

In one embodiment, all or a portion of the periphery of frame 202 is configured to be generally aligned with, or have a similar contour or shape as, frame assembly 12 of support assembly 10. In this was, fame 202 does not extend to areas where it may be less desirable to have relatively rigid components such as frame 202 and/or frame assembly 12. According to various alternative embodiments, frame 202 can have a variety of peripheral shapes and sizes (e.g., customized to a particular residual limb, to a particular support assembly configuration, etc.).

It should be understood that the components of lower support assembly 200 can be customized to a particular patient, and include various adjustability features such as, or similar to, those discussed with respect to support assembly 10. For example, intermediate portion 214 of frame assembly 202 may provide longitudinal and/or angular adjustment capabilities between upper portion 212 and lower portion 216. Similarly, pylon 204 may be longitudinally adjustable so as to accommodate height differences between patients ad/or particular residual limb types. Further yet, one or both of pylon 204 and artificial foot 206 can be replaceable/ exchangeable such that different sized components can be used to suit a particular application/patient. All such features and combinations of features are to be understood to be within the scope of the present disclosure.

Furthermore, while lower support assembly 200 is generally described herein as being used in connection with support assembly 10, it should be understood that according to various alternative embodiments, lower support assembly 200 is usable with a wide variety of support assemblies and similar devices including, for example, support assembly 110.

The various embodiments of the support assembly and/or lower support assembly shown and described herein may provide various benefits to users and have advantages over more typical post-operative support devices. For example, the frame adjustment features permit configuring the frame assembly to properly accommodate length and/or varus/ valgus (e.g., knock-knee and/or bow-legged) variations between patients. Further, such adjustment features permit the usage of the frame assembly and support assembly with either a right or left leg. Further yet, the separate side portions of the lower frame may provide improved support for the end of the residual limb (e.g., in the case of angled amputations, irregularities, swelling, etc.).

For purposes of this disclosure, the term "coupled" shall mean the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature. Such joining may also relate to a mechanical, fluid, or electrical relationship between the two components. Accordingly, all such modifications are intended to be included within the scope of the present disclosure as defined in the appended claims.

The construction and arrangement of the elements of the support assembly as shown in the exemplary embodiments are illustrative only. Although a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the embodiments. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. A post-operative residual limb support assembly comprising:
   a frame assembly comprising:
      an upper frame configured to extend about at least a portion of a residual limb, the upper frame including a first strap;
   a lower frame coupled to the upper frame and configured to receive an end of the residual limb, wherein the lower frame is coupled to the upper frame via an elongated connection member, the lower frame including a second strap;
   a liner assembly configured to be positioned between the frame assembly and the residual limb, the liner assembly comprises an upper liner removeably coupled to the upper frame and a lower liner removeably coupled to the lower frame, wherein the first strap is configured to compress the upper liner about the residual limb and the second strap is configured to compress the lower liner about the residual limb;
   a pylon coupled to the lower frame;
   wherein the upper frame and the lower frame are adjustable relative to one another in at least one of a linear and a rotational manner.

2. The post-operative residual limb support assembly of claim 1, wherein the upper frame includes a first recess and the lower frame includes a second recess, and wherein the connection member is at least partially received within the first and second recesses.

3. The post-operative residual limb support assembly of claim 2, wherein the first recess is configured to provide a predetermined amount of angular adjustment between the connection member and the upper frame, and wherein the second recess is configured to provide a predetermined amount of angular adjustment between the connection member and the upper frame, wherein the predetermined amount of angular adjustment is at least five degrees relative to a straight position.

4. The post-operative residual limb support assembly of claim 2, wherein the connection member and first and second recesses are configured to provide adjustability between the upper frame and the lower frame to correspond to varus/valgus variations between patients.

5. The post-operative residual limb support assembly of claim 1, wherein the connection member comprises a first slot configured to provide lengthwise adjustment between the connection member and the upper frame.

6. The post-operative residual limb support assembly of claim 1, wherein the connection member comprises a second slot configured to provide lengthwise adjustment between the connection member and the lower frame.

7. The post-operative residual limb support assembly of claim 1, wherein the connection member is configured to be deformed to provide for anterior/posterior angulation when the support assembly is secured to the residual limb.

8. The post-operative residual limb support assembly of claim 1, wherein the lower frame comprises a cup-shaped bottom configured to receive the end of the residual limb.

9. The post-operative residual limb support assembly of claim 8, wherein the cup-shaped bottom defines a slot dividing the cup-shaped bottom into first and second side portions.

10. The post-operative residual limb support assembly of claim 9, wherein the first and second side portions are independently deflectable to accommodate the shape of the end of the residual limb.

11. The post-operative residual limb support assembly of claim 10, wherein the first and second side portions are generally semi-spherical in shape.

12. The post-operative residual limb support assembly of claim 1, wherein the upper frame and lower frame are configured to be fixed in position relative to one another after the support assembly has been adjusted to fit the residual limb.

13. The post-operative residual limb support assembly of claim 1, wherein at least one of the upper frame, the lower frame, and the liner assembly comprises an elastic band configured to enable securing the support assembly to the residual limb.

14. The post-operative residual limb support assembly of claim 1, wherein at least one of the upper frame and the lower frame comprises a slot, and the other of the upper frame and the lower frame comprises an aperture, such that a fastener extends through the slot and the aperture and permits lengthwise and angular adjustment of the upper frame relative to the lower frame.

15. The post-operative residual limb support assembly of claim 1, wherein the support assembly is usable with either a left leg or a right leg.

16. The post-operative residual limb support assembly of claim 1, further comprising an artificial foot coupled to the pylon, wherein the pylon extends between the lower frame and the artificial foot.

17. The post-operative residual limb support assembly of claim 1, wherein the frame assembly is formed at least in part of a metal or a composite material.

18. A post-operative residual limb support assembly comprising:

a frame assembly comprising:

an upper frame configured to extend about at least a portion of a residual limb;

a lower frame coupled to the upper frame and configured to receive an end of the residual limb;

a liner assembly configured to be positioned between the frame assembly and the residual limb, the liner assembly comprises an upper liner removeably coupled to the upper frame and a lower liner removeably coupled to the lower frame;

a pylon coupled to and extending from the lower frame;

wherein the upper frame and the lower frame are adjustable relative to one another in a linear manner and a rotational manner, wherein the upper frame and the lower frame are adjustable relative to one another in the rotational manner by at least five degrees relative to a straight position;

wherein at least one of the upper frame and the lower frame comprises a slot, and the other of the upper frame and the lower frame comprises an aperture, such that a fastener extends through the slot and the aperture and permits lengthwise and angular adjustment of the upper frame relative to the lower frame.

19. The post-operative residual limb support assembly of claim 18, further comprising an artificial foot coupled to the pylon, wherein the pylon extends between the lower frame and the artificial foot.

20. A post-operative residual limb support assembly comprising:

a frame assembly comprising:

an upper frame configured to extend about at least a portion of a residual limb;

a lower frame coupled to the upper frame and configured to receive an end of the residual limb, wherein the lower frame comprises a cup-shaped bottom configured to receive the end of the residual limb, wherein the cup-shaped bottom defines a slot dividing the cup-shaped bottom into first and second side portions, wherein the first and second side portions are independently deflectable to accommodate the shape of the end of the residual limb;

a liner assembly configured to be positioned between the frame assembly and the residual limb, the liner assembly comprises an upper liner removeably coupled to the upper frame and a lower liner removeably coupled to the lower frame;

a pylon extending from the lower frame;

wherein the upper frame and the lower frame are adjustable relative to one another in at least one of a linear and a rotational manner.

21. The post-operative residual limb support assembly of claim 20, wherein the first and second side portions are generally semi-spherical in shape.

22. The post-operative residual limb support assembly of claim 20, further comprising an artificial foot coupled to the pylon, wherein the pylon extends between the lower frame and the artificial foot.

* * * * *